United States Patent
Urich (12)

(10) Patent No.: US 6,258,066 B1
(45) Date of Patent: Jul. 10, 2001

(54) INTRAVENOUS CATHETER STABILIZING DEVICE

(76) Inventor: Rex W. Urich, 326 Sonora Dr., San Mateo, CA (US) 94402

( * ) Notice: Subject to any disclaimer, the term of this patent is extended or adjusted under 35 U.S.C. 154(b) by 0 days.

(21) Appl. No.: 09/264,601

(22) Filed: Mar. 8, 1999

(51) Int. Cl.[7] ...................................................... A61M 5/32
(52) U.S. Cl. ........................ 604/174; 604/179; 604/180
(58) Field of Search ..................... 604/174, 177, 604/178, 179, 180; 128/DIG. 26; 119/712, 856

(56) References Cited

U.S. PATENT DOCUMENTS

| | | | |
|---|---|---|---|
| 3,812,851 | 5/1974 | Rodriguez | 128/133 |
| 4,088,136 | 5/1978 | Hasslinger et al. | 128/349 |
| 4,397,647 | 8/1983 | Gordon | 604/180 |
| 4,416,664 | 11/1983 | Womack | 604/174 |
| 4,490,141 * | 12/1984 | Lacko et al. | 604/180 |
| 4,583,976 | 4/1986 | Ferguson | 604/174 |
| 4,591,356 | 5/1986 | Christie | 604/179 |
| 4,612,925 | 9/1986 | Bender | 128/133 |
| 4,671,787 | 6/1987 | Widman | 604/179 |
| 4,726,716 | 2/1988 | McGuire | 604/180 |
| 4,945,925 | 8/1990 | Garcia | 128/877 |
| 4,976,698 | 12/1990 | Stokley | 604/174 |
| 4,981,475 | 1/1991 | Haindl | 604/174 |
| 5,076,289 | 12/1991 | Darling | 128/877 |
| 5,188,608 | 2/1993 | Fritts | 604/179 |
| 5,342,317 | 8/1994 | Claywell | 604/179 |
| 5,354,282 * | 10/1994 | Bierman | 604/180 |
| 5,403,285 | 4/1995 | Roberts | 604/179 |
| 5,413,562 * | 5/1995 | Swauger | 604/179 |
| 5,480,719 | 1/1996 | Tollini | 428/345 |
| 5,549,567 * | 8/1996 | Wolman | 604/179 |
| 5,577,516 | 11/1996 | Schaeffer | 128/877 |
| 5,722,959 * | 3/1998 | Bierman | 604/174 |
| 5,728,053 | 3/1998 | Calvert | 602/5 |
| 5,810,781 | 9/1998 | Bierman | 604/174 |
| 5,830,184 | 11/1998 | Basta | 604/104 |
| 5,839,393 * | 11/1998 | Rupp et al. | 119/712 |

\* cited by examiner

Primary Examiner—Glenn K. Dawson
Assistant Examiner—Jennifer Maynard
(74) Attorney, Agent, or Firm—Meyer Intellectual Property Law; Virginia H. Meyer, Esq.; Mark J. Spolyar, Esq.

(57) ABSTRACT

The present invention provides a new intravenous catheter stabilizing device comprising a disposable catheter assembly and a reusable strap having a hole or aperture therein. The catheter assembly includes a hub portion and a catheter, as is conventional in the art. The aperture or hole in the strap is configured such that the hub of a catheter assembly may extend at least partially therethrough. The strap of the present invention has attachment means located thereon and proximal to the aperture for attaching the catheter assembly to the strap such that the hub portion of the catheter assembly extends at least partially through the aperture of the strap. The strap further includes fastening means for securing the strap around a limb of a patient. When the device of the present invention is assembled and used as intended on a limb of a patient, the hub of the catheter partially extends through the aperture in the strap thereby allowing attachment of an intravenous tube with a standard luer lock mechanism. In this configuration, the device protects the attached catheter hub and secures it against the limb of a patient and adjacent to the venipuncture site.

21 Claims, 7 Drawing Sheets

INTRAVENOUS CATHETER STABILIZING DEVICE

FIELD OF THE INVENTION

The present invention relates to intravenous catheter stabilizing devices which support and protect catheters inserted into a human or animal patient. More particularly, the present invention relates to a catheter stabilizing device having a reusable strap assembly and a disposable catheter assembly, which in combination secure and protect a catheter hub adjacent to a venipuncture site.

BACKGROUND OF THE INVENTION

A venipuncture can be made in many areas of the human body, such as the forearm, upper arm, or leg. In veterinary medicine, venipuncture is usually performed on a forelimb of the animal patient. In a typical venipuncture procedure, a catheter is inserted into a vein by means of a hollow needle which is then withdrawn to avoid damage to the walls of the punctured vein. The catheter remains in the vein of the patient and is connected to a source of infusion liquid. It is then necessary to stabilize the catheter to prevent movement which may work the catheter loose and create a potential source of infection or irritation to the patient at the point of catheter insertion. This stabilization is generally done by taping the catheter hub and associated tube fittings to the patient's skin in an area adjacent to the point of catheter insertion.

Although it is important to obtain secure stabilization of the inserted catheter or needle, use of adhesive tape is not always desirable. For example, repeated application and removal of adhesive tape from the skin of a long-term patient may damage the skin of the patient and be quite painful. The use of such adhesive tapes is also quite time-consuming, requiring that strips of adhesive tape or similar materials be individually cut and trimmed to fasten the IV catheter directly to the skin of a patient or animal. Time consumption becomes a larger factor in situations where the adhesive tape must be frequently changed. Changes in swelling conditions of the limb in which the catheter is placed exacerbate these problems as they often require re-stabilization of the inserted catheter with new adhesive. Moreover, in some circumstances, the condition of the skin may prevent proper adhesion of the adhesive strips.

Additionally, catheterization of an animal patient presents additional problems. A canine, for example, who has been catheterized often attempts to chew at the catheterization site. Prior art techniques that use adhesives are generally insufficient to protect the inserted catheter. Accordingly, as to veterinary applications, there is an especial need to secure inserted IV catheters and to prevent the animal patient from chewing or otherwise disturbing the catheter.

Accordingly, there has been a need for a novel catheter stabilizing device which secures and protects a catheter hub or a syringe body adjacent to a venipuncture site. The need exists for such a catheter stabilizing device to be of simplified construction, inexpensive to manufacture, and easily understood and used by medical and veterinary personnel. Additionally, a catheter stabilizing device is needed which may be readily attached to or detached from the patient without the use of adhesives. Moreover, a need exists for such a catheter stabilizing device which is easy to place upon the limb of the patient, and is adapted to hold not only the catheter hub assembly, but also the tubes feeding fluid to the venipuncture site. The present invention fulfills these needs and provides other related advantages.

SUMMARY OF THE INVENTION

The present invention provides a new intravenous catheter stabilizing device comprising a disposable catheter assembly and a reusable strap having a hole or aperture therein. The catheter assembly includes a hub portion and a catheter, as is conventional in the art. The aperture or hole in the strap is configured such that the hub portion of a catheter assembly may extend at least partially therethrough. The strap of the present invention has attachment means located thereon and proximal to the aperture for attaching the catheter assembly to the strap such that the hub portion of the catheter assembly extends at least partially through the aperture of the strap. The strap further includes fastening means for securing the strap around a limb of a patient. When the device of the present invention is assembled and used as intended on a limb of a patient, the hub of the catheter partially extends through the aperture in the strap thereby allowing attachment of an intravenous tube with a standard luer lock mechanism. In this configuration, the device protects the attached catheter hub and secures it against the limb of a patient and adjacent to the venipuncture site.

One aspect of the present invention features catheter attachment assemblies which hold a standard catheter assembly and present features for securement to the strap of the present invention. Embodiments according to this aspect of the present invention include adhesive strips and flexible plastic members which secure a standard catheter assembly and present attachment sites for corresponding attachment means located on the strap of the invention. Other catheter attachment assemblies of the present invention include features integral with the catheter hub for attachment to the strap. One such embodiment is an injection-molded part comprising two opposing, flexible tabs extending from a catheter hub. These opposing tabs each have snap elements located thereon corresponding to mating snap elements on the strap. Another embodiment according to this aspect of the invention comprises a catheter assembly with a groove in its hub portion that corresponds to a U-shaped clip located on the strap.

More specifically and in one preferred embodiment, the present invention is an intravenous catheter stabilizing device generally comprising a reusable strap and a disposable catheter attachment assembly. The catheter attachment assembly includes a catheter assembly having a hub portion and a needle. The catheter attachment assembly further includes at least one feature which allows for its attachment to the strap of the present invention. In one preferred embodiment, these features comprise opposing, flexible tabs having snap elements located thereon. The strap has an aperture and two mating snap elements located on opposite sides of the aperture. The mating snap elements of the strap correspond to the snap elements of the catheter attachment assembly. The aperture has a diameter sufficient to permit passage of the catheter hub therethrough. Lastly, the strap has securing means which releasably attaches the strap to itself to securely hold the strap over the venipuncture site and around the limb of a patient. The catheter stabilizing device of the present invention stabilizes the inserted catheter at the venipuncture site. Furthermore, the strap of the present invention also covers and protects the otherwise exposed catheter hub.

In actual use, the catheter attachment assembly is inserted into the vein of a patient by means of a hollow needle as is conventional in the field. The hollow needle is withdrawn leaving the catheter inserted into the vein and the catheter hub lying adjacent to the venipuncture site. The catheter attachment assembly is then coupled to the reusable strap at the attachment site such that the hub partially extends through the hole of the strap. Lastly, the strap is wrapped around the limb of the patient and secured to itself thereby stabilizing the catheter relative to the venipuncture site. A tube carrying desired intravenous fluids can then be attached to the catheter hub. Alternatively, the tube can be attached to the catheter hub before the strap is wrapped and secured around the patient's limb.

The catheter attachment assembly of the present invention encompasses many different embodiments. The catheter attachment assembly includes a standard catheter assembly having a catheter and a hub portion. The catheter may comprise TEFLON, polyethylene, polypropylene, or any other suitable plastic. The catheter is attached to the hub portion in a conventional manner. The catheter hub portion may similarly be made of any suitable plastic. The present invention contemplates various shapes for the catheter hub portion each of which are adapted for attachment to the strap of the present invention. For example, the catheter hub portion may have tabs or wings which extend from the hub. These tabs may include an attachment feature to which a mating feature located on the strap attaches. As the various drawings indicate, such attachment features may include a snap assembly or an area of Velcro®-type hook or loop fasteners. Furthermore, other catheter hub shapes for use in the present invention include a groove formed about the circumference of the catheter hub portion that cooperates with a clip located proximal to the aperture in the strap.

Still further, the strap of the present invention may be used with a standard catheter assembly. In this configuration, the strap includes a clip or other member located proximal to the aperture which grips the hub portion of the catheter assembly and presents the remainder of the hub portion at the aperture of the strap for attachment of an IV tube.

The strap of the present invention may be made of any suitable pliable material, including, but not limited to, nylon, polyester, canvas, cotton, and the like. The strap of the present invention includes a hole or aperture therethrough. The aperture may be located anywhere along the strap as desired. In a preferred form, the aperture appears near an end portion of the strap. The size of the hole or aperture is configured such that the hub portion of a catheter assembly may extend at least partially therethrough. The size of the aperture must only be large enough to permit the attachment of an IV tube to the catheter hub by any standard means, including a luer lock. The strap must be of sufficient length to wrap around the limb of a patient. In preferred form, the length of the strap is sufficient to permit the strap to wrap around the limb of a patient and cover the aperture located in the strap. Naturally, larger limbs require longer straps. The strap of the present invention further includes means to secure itself around the limb of a patient. In preferred form, such means comprises VELCRO®-type fasteners located on the inner and outer surfaces of the strap. Other means may include an array of snaps, hooks and the like.

In yet other embodiments, the strap may comprise a U-shaped assembly of either composite or unitary construction. The two legs of the U-shaped strap both wrap around the limb of a patient. The second strap of this configuration adds further support to the catheter stabilizing device of the present invention.

By way of example and according to one teaching of the invention, the intravenous catheter stabilizing device of the present invention may include a disposable catheter attachment assembly and a reusable strap having a hole therein. The catheter attachment assembly of this embodiment has a catheter and a hub portion. The hub portion has opposing tabs extending therefrom. Each opposing tab has a snap element located thereon. The reusable strap of the present invention, as described, has a hole proximally located on the end of the strap. The reusable strap further has two mating snap elements located on opposite sides of the hole in the strap. The distance between the snap elements of the catheter attachment assembly corresponds to the distance between the mating snap elements of the strap such that the catheter attachment assembly can be releasably secured to the strap.

Furthermore, the strap also has a VELCRO®-type fastening means comprised of a plurality of engaging elements on its inner surface (the surface which contacts the skin of a patient) and a second plurality of mating engaging elements on the outer surface of the strap which together provide the means by which the strap is secured around a limb of a patient. The VELCRO® hooks and loops, respectively, can be placed on either the inner or outer surface of the strap as desired. Of course, any suitable engaging elements may be used to securely hold the strap in place, including, but not limited to, snaps, hooks, adhesives, and the like. However, in veterinary applications, a preferred embodiment features a strap wherein VELCRO® hooks are located on the inner, skin contacting surface of the strap and the VELCRO® loops are located on the outer surface. In this configuration, the VELCRO hooks on the inner surface of the strap engage the animals fur to help prevent the strap from slipping.

Before explaining preferred embodiments of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIGS. 1A and 1B.

FIGS. 2A and 2B.

FIGS. 6A and 6B.

FIGS. 7A and 7B.

FIGS. 9A and 9B; FIG. 9A is a top plan view of the injection molded catheter attachment assembly in accordance with a fourth preferred embodiment; and, FIG. 9B is a front elevation view of the injection molded catheter attachment assembly of the fourth preferred embodiment.

FIGS. 10A, 10B, and 10C.

FIGS. 11A and 11B; FIG. 11A is a top plan view of the strap of a fourth preferred embodiment; and, FIG. 11B is a side elevation view of the strap of the fourth preferred embodiment.

The same reference numerals refer to the same parts throughout the various Figures.

DESCRIPTION OF A FIRST PREFERRED EMBODIMENT

FIGS. 1A through 3 depict a first preferred intravenous catheter stabilizing device embodying the principles and concepts of the present invention. The first preferred embodiment generally comprises strap 10a and catheter attachment assembly 80a.

Figure 1A:
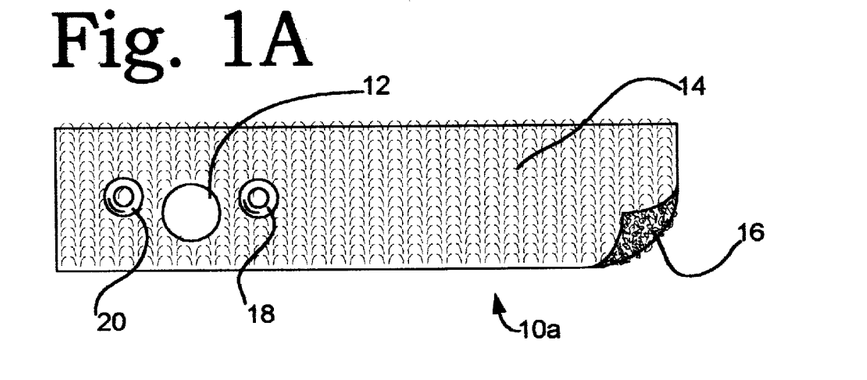
FIG. 1A is a top plan view of the strap in accordance with a first preferred embodiment of the present invention; and, FIG. 1B is a side elevation view of the strap in accordance with the first preferred embodiment.
Figure 1B:
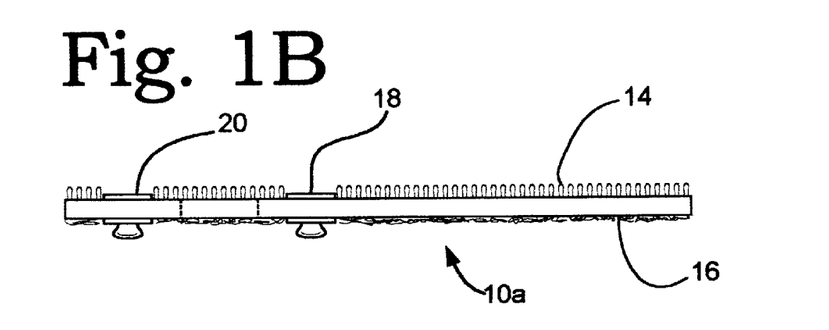

Strap 10a includes inner surface 16 and outer surface 14 (See FIGS. 1A and 1B). As FIGS. 1A and 1B indicate, strap 10a includes an area of VELCRO® hooks on inner surface 16 and an area of VELCRO® loops on outer surface 14. Additionally, Strap 10a has an aperture 12 located at a first end that extends through strap 10a. Aperture 12 is configured to allow catheter hub 88 to at least partially extend through. Strap 10a further includes male snap elements 18 and 20 placed adjacent to and on opposite sides of aperture 12. Strap 10a may comprise any kind of flexible strap material, including a cotton strap, nylon strap, polyester strap and the like. The first preferred embodiment features a nylon strap.

Figure 2A:
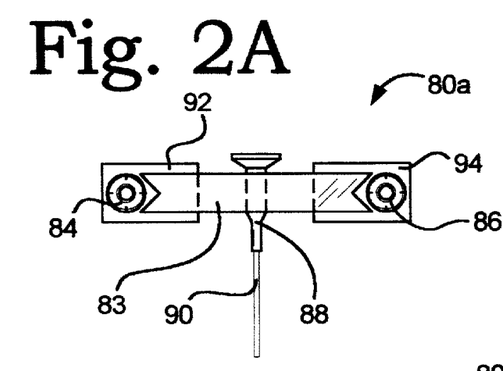
FIG. 2A is a top plan view of the catheter attachment assembly of the first preferred embodiment of the present invention; and, FIG. 2B is a rear elevation view of the catheter attachment assembly of the first preferred embodiment.
Figure 2B:
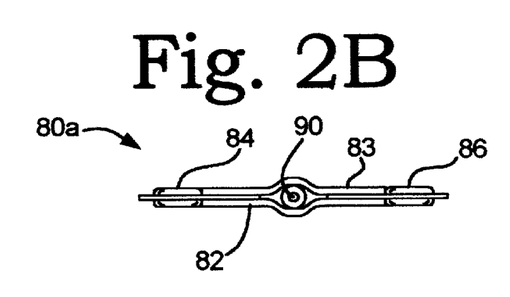

With reference to FIGS. 2A and 2B, catheter attachment assembly 80a comprises flexible adhesive strips 82 and 83, tabs 92 and 94, and female snap elements 84 and 86. Flexible adhesive strips 82 and 83 secure a standard catheter assembly 80a having a catheter hub 88 and a catheter 90 such that tabs 92 and 94 extend radially from catheter hub 88 between adhesive strips 82 and 83. As FIGS. 2A and 2B illustrate, female snap elements 84 and 86 attach to tabs 92 and 94.

As alluded to above, the first preferred embodiment may be used with a standard catheter assembly. To assemble the catheter attachment assembly for use, the user positions tab 92 on adhesive strip 82 such that the center line of tab 92 is aligned with the center line of adhesive strip 82. The user positions tab 94 in a similar fashion on the opposite end of adhesive strip 82. The user then places catheter hub 88 in the center of adhesive strip 82. To complete the assembly, a second adhesive strip 83 is then secured to the opposite sides of tabs 92 and 94. Tabs 92 and 94 comprise a flexible plastic material such that they flex with the patient's movements.

As one may readily recognize, male snap elements 18 and 20 and female snap elements 84 and 86 may comprise any kind of material including metal, plastic, and the like. Furthermore, the respective locations of the female and male snap elements may be switched. In this configuration, strap 10a includes male snap elements and catheter attachment assembly 80a includes female snap elements. Furthermore, second adhesive strip 83 may have adhesive on both surfaces. In this configuration, one adhesive surface helps to secure the catheter assembly relative to tabs 92 and 94, while the other adhesive surface can be applied to the skin of the patient thereby providing further stabilization of the catheter assembly relative to the venipuncture site.

In use, the user assembles the catheter attachment assembly 80a as described above. The catheter 90 is then placed in the vein of a patient by any conventional means. After catheter 90 is inserted into the vein, the user attaches strap 10a to catheter attachment assembly 80a. More specifically, female snap elements 84 and 86 of strap 10a engage and releasably couple to male snap elements 18 and 20 of catheter attachment assembly 80a. Strap 10a is then wrapped around the limb of the patient and secured in place by VELCRO® fasteners. More specifically, the user contacts inner surface 16 against outer surface 14 to thereby secure strap 10a in the area between the end of the strap and aperture 12. The user secures an IV tube to hub portion 88 in a conventional manner and contacts the remainder of inner surface 16 against outer surface 14 of strap 10a to thereby cover aperture 12, catheter hub 88, and the attached IV tube. This configuration finds especial use in veterinary applications since it prevents an animal patient from successfully chewing at or otherwise disturbing the attachment of the IV tube 91 and the catheter hub 88.

Strap 10a is at least as long as is necessary to completely extend around the patient's limb. As discussed above, strap 10a is configured such that it overlaps itself and covers aperture 12 (See FIG. 3). As will be recognized, the VEL-CRO® fasteners may also comprise other appropriate fastening devices including, snap elements, hooks, laces that tie together, elastic and the like.

Figure 3:
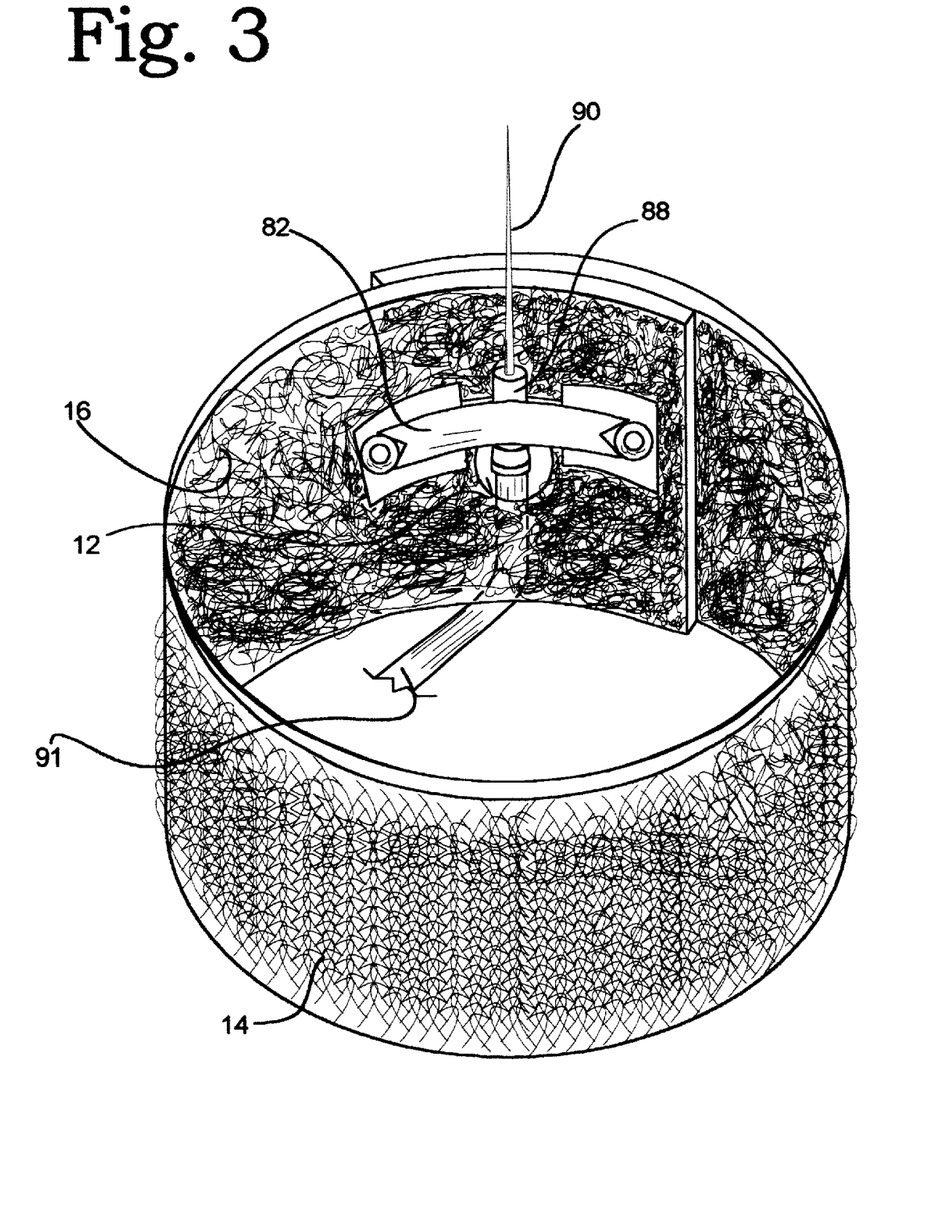
FIG. 3 is an isometric view of the first preferred embodiment illustrating the attachment of the strap to the catheter attachment assembly.
Figure 4:
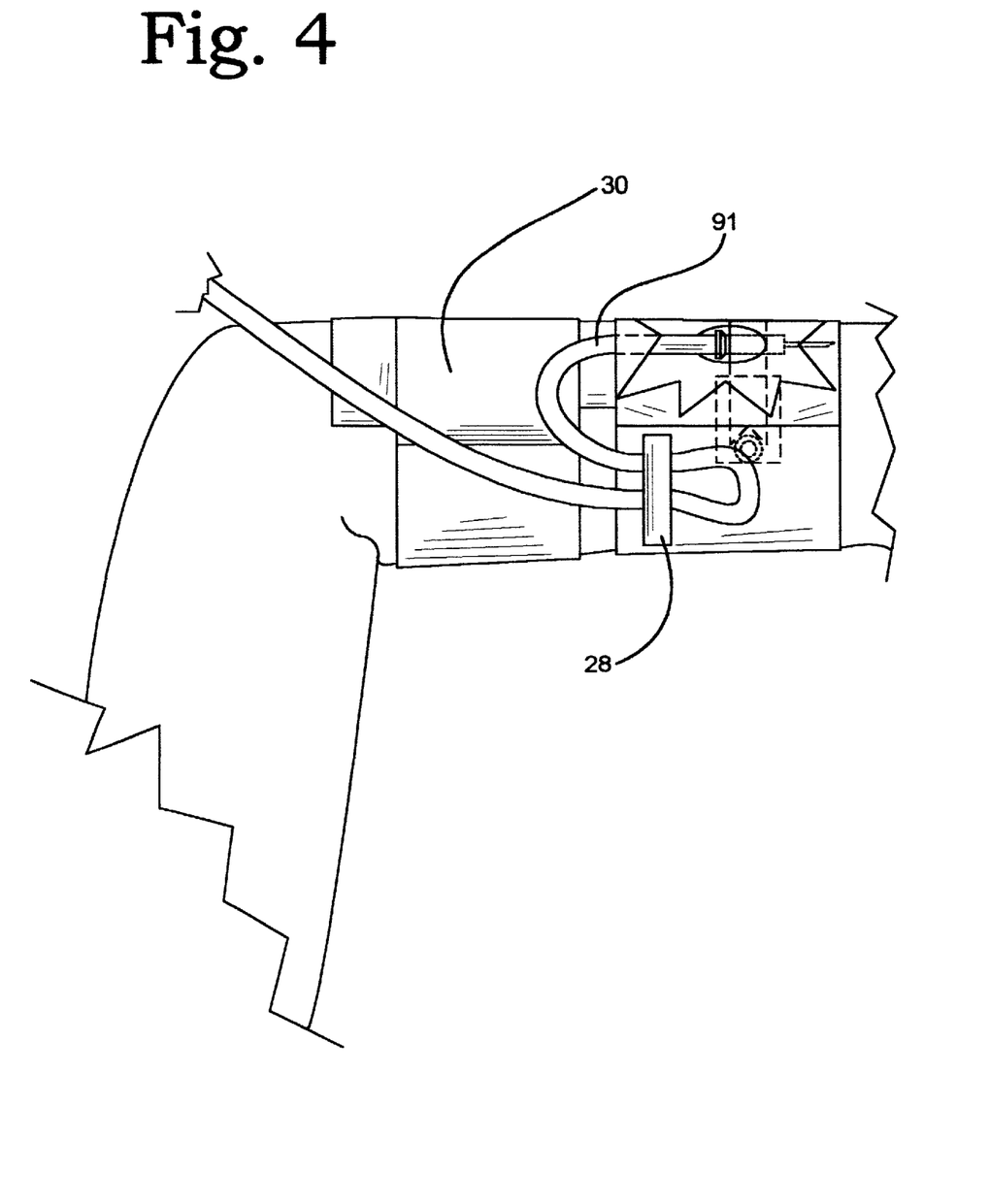
FIG. 4 is an isometric view of a second preferred embodiment of the present invention as applied to a patient's arm.

As shown in FIG. 3, catheter attachment assembly 80a and aperture 12 of strap 10a are positioned such that catheter hub 88 may at least partially extend through aperture 12 of strap 10a. In this configuration, catheter hub 88 is presented at aperture 12 for attachment of an intravenous tube 91. Furthermore, as shown in FIG. 3, strap 10a overlaps itself to cover aperture 12 and catheter hub 88 to protect against unintentional detachment of IV tube 91 from catheter hub 88. This overlapped strap configuration also prevents an animal patient from chewing at the catheter hub and IV tube attachment.

Figure 10A:
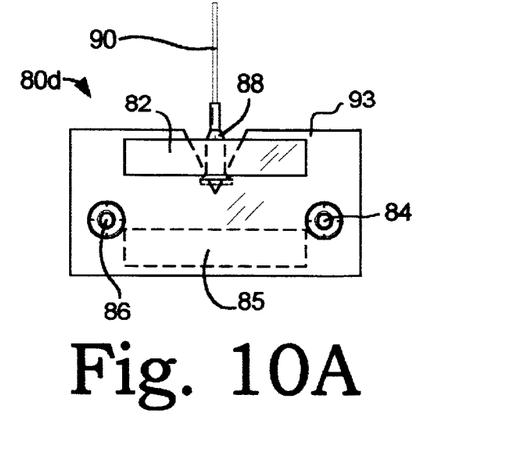
FIG. 10A is a top plan view of an alternative catheter attachment assembly for use with the strap of either the first or second preferred embodiments.
Figure 10B:
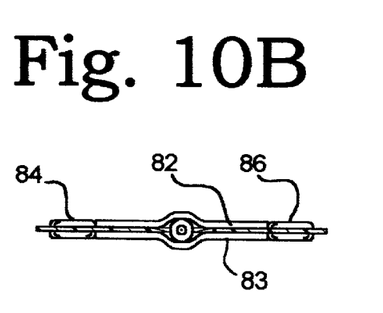
FIG. 10B is a front elevation view of the alternate catheter attachment assembly; and, FIG. 10C is a rear elevation view of the alternate catheter attachment assembly.
Figure 10C:
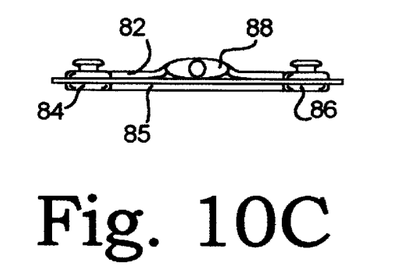

In addition, FIGS. 10A thru 10C show an alternative catheter attachment assembly 80d for use with strap 10a. Catheter attachment assembly 80d comprises a thin flexible card-like member 93, male snap elements 84 and 86, and adhesive strips 82 and 83. Of course, the use of male snap elements 84 and 86 on the catheter attachment assembly 80d requires that strap 10a include corresponding female snap elements in place of male snap elements 18 and 20, as shown in FIG. 1A. The thin card 93 is made of a flexible or supple material such as plastic, rubber, cotton and the like. A notch is cut out from the center, middle edge of thin flexible card 93 in order to accommodate catheter hub 88. As shown in FIGS. 10A and 10C, catheter hub 88 rests on the upper surface of card-like member 93.

To make catheter attachment assembly 80d, the user places first adhesive strip 82 over the notch and secures its ends to card 93 on either side of the notch. The user then places catheter hub 88 on first adhesive strip 82 in the area exposed by the notch, and finally places second adhesive strip 83 on the opposite side of card 93 and directly over first adhesive strip 82. Catheter attachment assembly 80d may further include adhesive strip 85 for adhesion to the patient's skin to provide further stabilization of catheter attachment assembly 80d.

Additionally, as can be seen from the descriptions provided above, the catheter attachment assemblies are preferably flexible in overall construction. A flexible catheter attachment assembly bends and moves as the patient moves, leaving the inserted catheter substantially in place. A rigid catheter attachment assembly may, in some circumstances, increase the risk of the catheter being removed unintentionally from the vein, as the patient moves his or her limb.

DETAILED DESCRIPTION OF THE SECOND PREFERRED EMBODIMENT

FIGS. 4 thru 6B illustrate a second preferred embodiment of the intravenous catheter stabilizing device embodying the principles and concepts of the present invention. As above, the second preferred embodiment generally comprises strap assembly 10b and catheter attachment assembly 80b.

Figure 5:
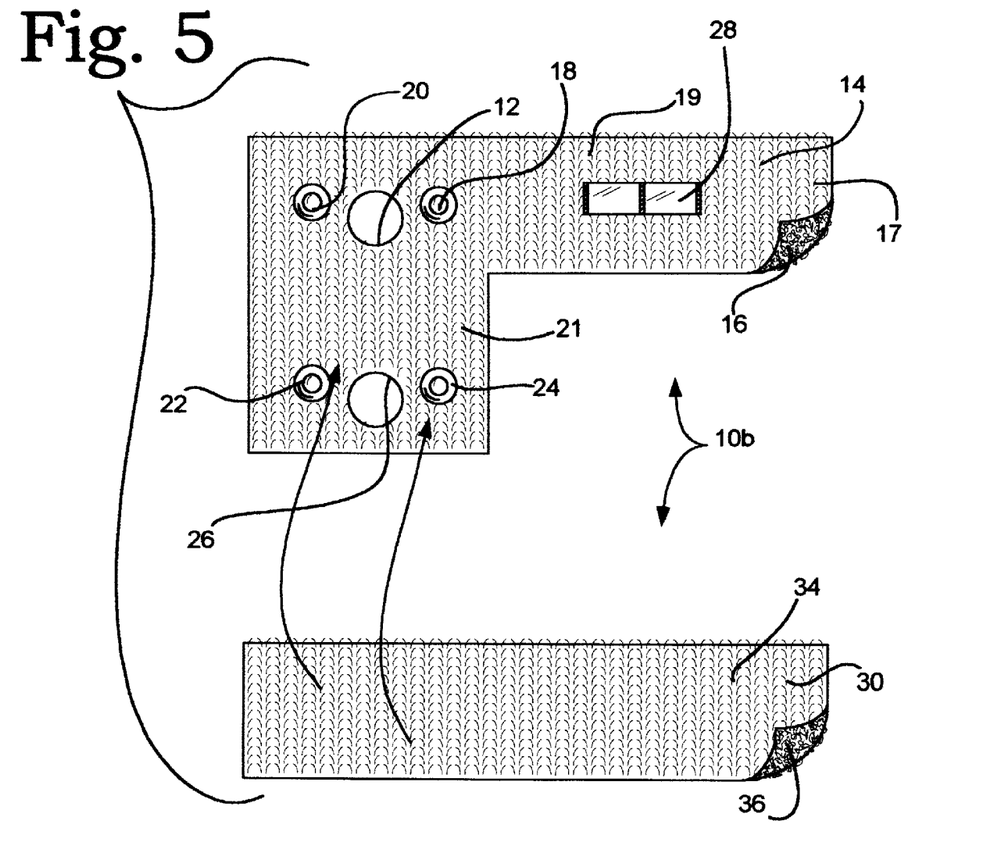
FIG. 5 is a top plan view of the U-shaped strap assembly of the second preferred embodiment.

As shown in FIG. 5, strap assembly 10b comprises a first L-shaped strap 17 having first leg 19 and second leg 21 and a second strap 30. First strap 17 has inner surface 16 and outer surface 14. Second strap has inner surface 36 and outer surface 34. Additionally, strap 17 further has a first aperture 12, male snap elements 18 and 20, and IV tube stress relief band 28. Strap 17 may further include a second aperture 26 and male snap elements 22 and 24.

First aperture 12 and second aperture 26 are each configured to allow a catheter hub to extend at least partially therethrough. Male snap elements 18 and 20 are positioned on opposite sides of aperture 12. Male snap elements 22 and 24 are similarly positioned relative to aperture 26. Aperture 26 allows for stabilization of a catheter assembly at a second venipuncture site without substantial movement of strap assembly 10b.

Figure 6A:
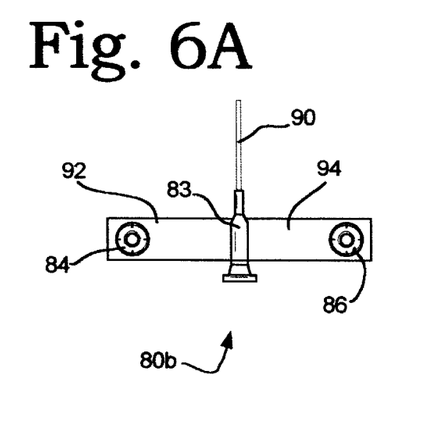
FIG. 6A is a top plan view of the catheter attachment assembly of the second preferred embodiment featuring an injection-molded assembly; and, FIG. 6B is a front elevation view of the injection molded catheter attachment assembly of the second preferred embodiment.
Figure 6B:
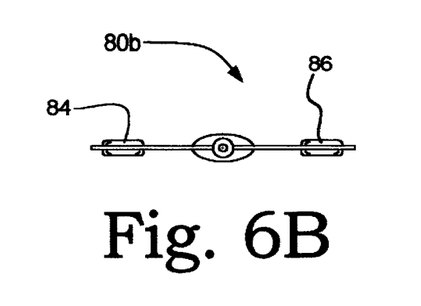

As FIGS. 6A and 6B indicate, catheter attachment assembly 80b is of unitary construction. More specifically, catheter attachment assembly 80b is an injection molded part including catheter 90, catheter hub 88 and opposing tabs 92 and 94. As shown in FIGS. 6A and 6B, opposing tabs 92 and 94 extend radially from catheter hub 88. Female snap elements 84 and 86 attach to tabs 92 and 94 respectively. Alternately, female snap elements 84 and 86 may be formed on opposing tabs 92 and 94 during the injection molding process, thereby obviating the need for the separate attachment of conventional snap elements.

The U-shaped configuration of strap assembly 10b is designed for enhanced stabilization of a catheter assembly adjacent to a venipuncture site. After a catheter attachment assembly 80b is inserted into a patient's vein and fixed in place by L-shaped strap 17, second strap 30 attaches to the second leg 21 of first strap 17 as indicated in FIG. 5. More specifically, inner surface 36 of second strap 30 attaches to outer surface 14 of L-shaped strap 17. Second strap 30 extends around the patient's limb and attaches to itself as is convention. In this manner, second strap 30 provides additional stability.

First leg 19 of first strap 17 and second strap 30 are at least as long as is necessary to completely pass around the patient's limb until a sufficient overlap is achieved. Second strap 30 is for additional support to fix strap assembly 10b to the patient's arm. Additionally, when a second catheter attachment assembly 80b is attached to strap assembly 10b, strap 30 will further cover the second catheter attachment assembly 80b to prevent accidental detachment of IV tube 91.

As will be recognized, it is not necessary for strap 30 and strap assembly 10b to be separate elements. Strap 30 and strap 17 may be of unitary construction to form a U-shaped strap assembly that attaches to a patient's arm in a manner substantially identical to that described above.

Additionally, strap assembly 10b may further include stress relief means 28 in order to prevent accidental displacement of the catheter caused by pulling the IV tube 91. Such stress relief means 28 also prevents tension placed on IV tube 91 to be transferred to catheter attachment assembly 80b. To that end, stress relief means 28 is a simple band of material attached to the outer surface of strap assembly 10b. Alternatively, any suitable stress relief means designed to secure a portion of IV tube 91 may be used, including those described in U.S. Pat. No. 5,577,516 issued to Schaeffer on Nov. 26, 1996; U.S. Pat. No. 5,342,317 issued to Claywell on Aug. 30, 1994; U.S. Pat. No. 5,480,719 issued to Tollini on Jan. 2, 1996; and, U.S. Pat. No. 5,810,781 issued to Bierman on Sep. 22, 1998.

Otherwise, the configuration and assembly of the second preferred embodiment is substantially the same as the first preferred embodiment. Reference, therefore, should be made to the description of the first preferred embodiment for further details of construction and assembly.

DETAILED DESCRIPTION OF THE THIRD PREFERRED EMBODIMENT

Figure 7A:
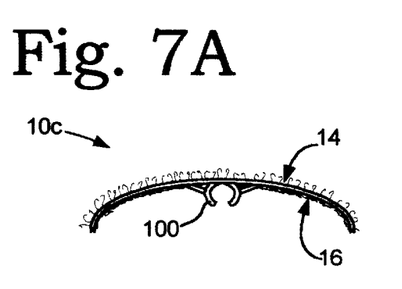
FIG. 7A is a front elevation view of a third preferred embodiment featuring a u-shaped clip on the strap for attachment of a catheter assembly; and, FIG. 7B illustrates the attachment of a catheter assembly to the u-shaped clip of the third preferred embodiment.
Figure 7B:
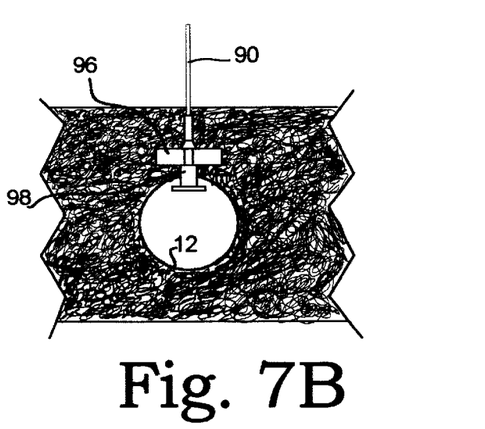
Figure 8:
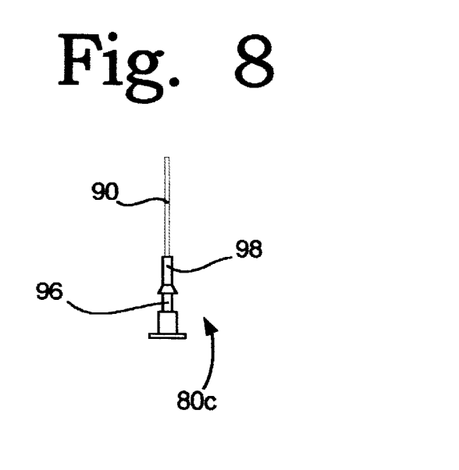
FIG. 8 is a top plan view of the grooved catheter hub and catheter in accordance with the third preferred embodiment.

FIGS. 7 and 8 show a third preferred embodiment of the present invention. The third preferred embodiment comprises, generally, strap 10c having a U-shaped clip 100, and a catheter assembly 80c having a grooved catheter hub 98.

Strap 10c of the third preferred embodiment is quite similar to the strap of the first preferred embodiment and includes inner surface 16 and outer surface 14. Additionally, strap 10c has aperture 12 located at a first end portion. Aperture 12 is configured to allow catheter hub 98 to extend at least partially therethrough.

Strap 10c further includes a U-shaped clip 100. U-shaped clip 100 is preferably designed to releasably engage groove 96 of catheter hub 98. As may readily be recognized, the U-shaped clip 100 may also be designed to releasably engage the hub of a standard catheter assembly.

Further, U-shaped clip 100 is located adjacent to aperture 12 of strap 10c such that a standard catheter hub or catheter hub 98 may be secured allowing catheter hub 98 to extend at least partially through aperture 12. Once the catheter 90 is inserted into a patient's vein, strap 10c is easily attached to catheter hub 98 with U-shaped clip 100. Strap 10c is then wrapped around and secured to the limb of a patient to thereby secure catheter hub 98 adjacent to the venipuncture site.

Otherwise, the configuration and assembly of the third preferred embodiment is substantially the same as the first preferred embodiment. Reference, therefor, should be made to the description of the first preferred embodiment.

DETAILED DESCRIPTION OF THE FOURTH PREFERRED EMBODIMENT

FIGS. 9A–B and 11A–B, illustrate a fourth preferred embodiment of the intravenous catheter stabilizing device featuring VELCRO® attachments for securing the catheter attachment assembly to the strap. As above, the fourth preferred embodiment generally comprises strap 10d and catheter attachment assembly 80e.

Figures 9A, 9B, 11A:
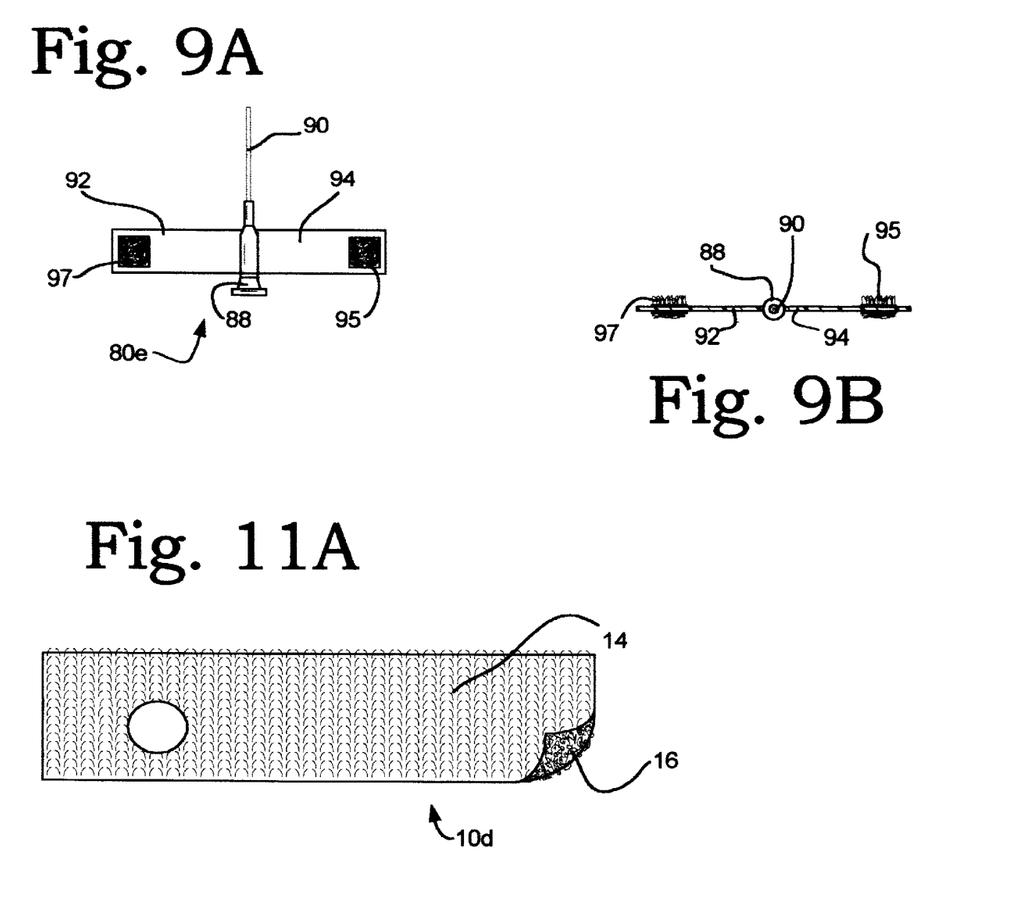
Figure 11B:
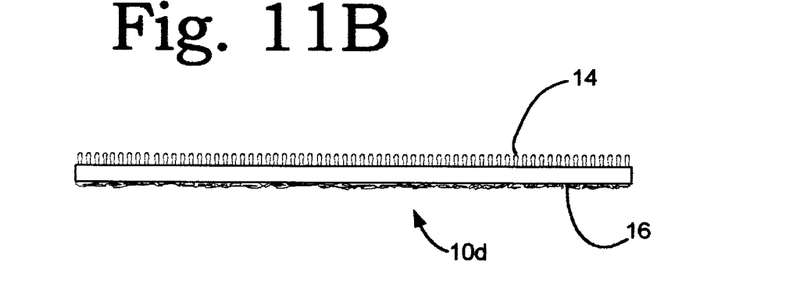

Unlike the strap of the first preferred embodiment, strap 10d does not include snap elements. Rather, inner surface 16 of strap 10d has a plurality of VELCRO®-type loop fasteners in the area surrounding aperture 12. Strap 10d also includes outer surface 14 and aperture 12 located at a first end portion. Aperture 12 is configured to allow catheter hub 88 at least partially extend through. Strap 10d may comprise any kind of flexible strap such as a cotton strap, nylon strap, polyester strap, and the like.

Catheter attachment assembly 80e is preferably an injection-molded part of unitary construction. As shown in FIGS. 9A and 9B, opposing tabs 92 and 94 extend radially from catheter hub 88. VELCRO® fasteners 95 and 97 are located at the end of each opposing tab 92 and 94 to attach to strap 10d thus replacing the snap elements of the first preferred embodiment.

In use, the user simply inserts catheter 90 into the patient's vein by any conventional means. VELCRO® hook fasteners 95 and 97 of respective opposing tabs 92 and 94 face away from the patient's limb and the venipuncture site and engage the VELCRO® loops of inner surface 16 of strap 10d. As described above, the user places catheter attachment assembly 80c relative to strap 10d such that catheter hub 88 extends at least partially through aperture 12. Strap 10d is wrapped and secured around the limb of a patient as previously described.

Otherwise, the configuration and assembly of the fourth preferred embodiment is substantially the same as the first preferred embodiment. Reference, therefore, should be made to the description of the first preferred embodiment.

SUMMARY

With respect to the above description, it is to be realized that the optimum dimensional relationships for the parts of the invention, including variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents fall within the scope of the invention.

What is claimed as being new and desired to be protected by Letters Patent of the United States is as follows:

1. An intravenous catheter stabilizing device comprising
   a catheter assembly having a hub portion and a catheter portion,
   a strap having an aperture therein through which said hub portion of said catheter assembly extends,
      said strap adapted to surround a limb of a patient;
      said strap further having fastening means for securing said strap around the limb of a patient, and
   attachment means located on said strap and proximal to said aperture for attaching said catheter assembly to said strap such that said hub portion extends at least partially through said aperture of said strap;
   wherein said attachment means comprises first and second snap elements,
   wherein said first and second snap elements are located proximal to said aperture and on opposite sides thereof,
   wherein said hub portion of said catheter assembly has first and second opposing tabs extending radially therefrom,
      wherein said first opposing tab has a first mating snap element,
      wherein said second opposing tab has a second mating snap element,
      wherein the distance between said first and second mating snap elements substantially matches the distance between said first and second snap elements of said strap.

2. The intravenous catheter stabilizing device of claim 1
   wherein said strap has a first inner surface and a second outer surface,
   wherein said fastening means comprises at least one engaging element located on said first inner surface of said strap and at least one mating engaging element located on said second outer surface of said strap.

3. The intravenous catheter stabilizing device of claim 1
   wherein said strap has a first end portion and a second end portion,
   wherein said strap has a first inner surface and a second outer surface,
   wherein said aperture is located on said first end portion of said strap,
   wherein said fastening means of said strap comprises at least one engaging element located on said first inner surface of said strap and at least one mating engaging element located on said second outer surface of said strap,
   wherein the length of said strap is such that said second end portion of said strap overlaps said first end portion of said strap and covers said aperture when said engaging element(s) attach(es) to said at least one mating engaging element.

4. The intravenous catheter stabilizing device of claim 1 further comprising a second strap,
   wherein said strap has a first inner surface and a second outer surface,
   wherein said second strap has at least one engaging element located on said first inner surface,
   wherein said second strap further has at least one mating engaging element located on said second outer surface,
   wherein said first strap is L-shaped having a first leg and a second leg,
   wherein said first leg is substantially perpendicular to said second leg,
   wherein said first strap has a first inner surface and a second outer surface,
   wherein said aperture and said attachment means are located on said first leg of said first strap, wherein said inner surface of said second strap attaches to said outer surface of said first strap at said second leg thereof.

5. The intravenous catheter stabilizing device of claim 4 wherein said first strap is integrally attached to said second strap.

6. The intravenous catheter stabilizing device of claim 4 or 5 further comprising second attachment means located on said second leg of said strap,
   wherein said second leg of said strap has an aperture therein located proximal to said second attachment means.

7. An intravenous catheter stabilizing device comprising
   a catheter assembly having a hub portion and a catheter portion,
   a strap having an aperture therein through which said hub portion of said catheter assembly extends,
      said strap adapted to surround a limb of a patient;
      said strap further having fastening means for securing said strap around the limb of a patient, and
   attachment means located on said strap and proximal to said aperture for positively attaching said catheter assembly to said strap such that said hub portion extends at least partially through said aperture of said strap; wherein said attachment means comprises a U-shaped clip having an inner engaging surface,
   wherein said inner engaging surface corresponds to at least a segment of the outer surface of said hub portion of said catheter assembly, and
   wherein said U-shaped clip engages said hub portion of said catheter assembly.

8. The intravenous catheter stabilizing device of claim 7, wherein said U-shaped clip releasably engages said hub of said catheter assembly.

9. The intravenous catheter stabilizing device of claim 8 or 7 wherein said hub portion of said catheter has a groove formed therein and extending around the circumference of said hub portion,
   wherein said U-shaped clip corresponds to said groove and engages said hub portion in said groove.

10. An intravenous catheter stabilizing device comprising
    a strap,
       said strap having a first inner surface and a second outer surface,
       said strap having an aperture therethrough,
       said strap further having an area of a plurality of loop fasteners on said second outer surface and an area of a plurality of hook fasteners on said first inner surface,
    and a catheter assembly having a hub portion and a catheter,
       wherein said hub portion of said catheter assembly has first and second opposing tabs extending radially therefrom,
          wherein said first opposing tab has a first area of a plurality of loop fasteners thereon,
          wherein said second opposing tab has a second area of a plurality of loop fasteners thereon,
    whereby the user inserts said catheter assembly into the vein of a patient with said first and second areas of loop fasteners facing away from the patient's skin, places said strap over said catheter assembly such that said hub portion extends at least partially through said aperture and such that said loop fasteners on said tabs of said catheter assembly engage said hook fasteners on said first inner surface of said strap.

11. An intravenous catheter stabilizing device comprising a thin, flexible card having a notch therein,
    said card having a first surface and a second surface,
    a first adhesive strip attached to said first surface of said flexible card and extending over said notch,
    a catheter assembly having a hub portion and a catheter,
       said hub portion of said catheter assembly positioned in said notch and contacting said adhesive strip,
    a second adhesive strip attached to said second surface of said flexible card extending over said notch and contacting said hub portion of said catheter assembly to thereby secure said hub portion to said card,
    said card further having a first snap element and a second snap element located on opposing sides of said notch,
    and a strap having an aperture therein and first and second mating snap elements on opposite sides of said aperture,
    said strap further having attachment means for securing said strap around the limb of a patient.

12. The intravenous catheter stabilizing device of claim 1 further comprising stress relief means located on said strap.

13. The intravenous catheter stabilizing device of claim 4 further comprising stress relief means located on said second strap.

14. The intravenous catheter stabilizing device of claim 1 further comprising a strip attached at the ends thereof to the outer surface of said strap, wherein said strip is adapted to secure an intravenous tube.

15. The intravenous catheter stabilizing device of claim 11 wherein said flexible card further includes adhesive on a surface thereof for contacting and adhering said flexible card to the skin of a patient.

16. The intravenous catheter stabilizing device of claims 4 wherein said first and second opposing tabs include adhesive on respective surfaces thereof for contacting and adhering said catheter assembly to the skin of a patient.

17. An intravenous catheter stabilizing device comprising
    a strap,
       said strap having a first inner surface and a second outer surface,
       said strap having an aperture therethrough,
       said strap further having a first snap element and a second snap element,
          said first and second snap elements located proximal to said aperture and on opposite sides thereof,
       said strap having an area of hook fasteners on said first inner surface and an area of loop fasteners on said second outer surface,
    a catheter assembly having a hub portion and a catheter portion, and first and second opposing tabs extending from said hub portion of said catheter assembly,
       said first opposing tab having a first mating snap element,
       said second opposing tab having a second mating snap element,
    wherein said first and second mating snap elements are spaced apart so as to releasably secure to said first and second snap elements on said strap.

18. The intravenous catheter stabilizing device of claim 17 wherein said first and second opposing tabs comprise thin, flexible plastic members.

19. An intravenous catheter stabilizing device comprising:
    a catheter holder comprising
       a flexible member having first and second snap elements at opposite ends thereof, and means for holding a catheter hub between said snaps elements;

a strap having an aperture therethrough and first and second mating snap elements located on opposite sides of said aperture and corresponding to said first and second snap elements on said flexible member;

said strap having a plurality of engaging members on one side thereof and a plurality of mating engaging members on the opposite side of said strap for securing said strap around a limb of a patient.

20. An intravenous catheter stabilizing device comprising:

a catheter holder comprising a first adhesive strip, a second adhesive strip, a first male snap assembly, a second male snap assembly and a catheter assembly having a hub portion and a catheter;

said first adhesive strip attached to said second adhesive strip with said catheter between and attached to said adhesive strips substantially at the midpoint of said strips;

said first male snap assembly attached to a respective end of said first and second strips;

said second male snap assembly attached to the opposite respective end of said strips;

a strap having an aperture therethrough; said strap further having first and second surfaces, and first and second female snap assemblies, said first and second female snap assemblies placed for engagement with said male snap assemblies of said catheter holder;

said aperture located between said first and second female snap assemblies and such that said catheter hub extends through said aperture when said female snap assemblies engage said male snap assemblies of said catheter holder;

and strap fastening means, said strap fastening comprising a hook area on said first surface and a loop(pile) area on said second surface to secure said strap around a limb of a patient.

21. The intravenous catheter stabilizing device of claim 20 further comprising a second strap said second strap having a first surface with a first area of pile fabric at one end of said second strap and a second area of pile fabric at the opposite end of said second strap;

said second strap having a second surface comprising an area of hooks;

wherein said first strap is L-shaped having a first longer member and a second shorter member, whereby said first pile area of said second strap attaches to said hook area of said shorter member of said first strap, wraps around a limb of a patient and, whereby said second pile area of said second strap contacts said hook area of said second strap to secure said second strap around said limb of said patient.

* * * * *